United States Patent [19]

Winicov

[11] Patent Number: 5,368,868

[45] Date of Patent: Nov. 29, 1994

[54] GERMICIDAL DETERGENT-IODINE COMPOSITIONS HAVING REDUCED DETERGENT CONTACT

[75] Inventor: Murray W. Winicov, Kansas City, Mo.

[73] Assignee: West Agro, Inc., Kansas City, Mo.

[21] Appl. No.: 163,596

[22] Filed: Dec. 6, 1993

Related U.S. Application Data

[63] Continuation of Ser. No. 947,041, Sep. 18, 1992, abandoned.

[51] Int. Cl.⁵ .............................................. A01N 59/12
[52] U.S. Cl. ...................................... 424/667; 514/947
[58] Field of Search ......................... 424/667; 514/947

[56] References Cited

U.S. PATENT DOCUMENTS

| | | | |
|---|---|---|---|
| 2,759,869 | 8/1956 | Sutton et al. | 424/672 |
| 3,028,299 | 4/1962 | Winicov et al. | 424/667 |
| 3,728,449 | 4/1973 | Cantor et al. | 424/667 |
| 4,271,149 | 6/1981 | Winicov et al. | 424/78.07 |

FOREIGN PATENT DOCUMENTS 1516653  7/1978  United Kingdom .

*Primary Examiner*—Marianne M. Cintins
*Assistant Examiner*—K. Weddington
*Attorney, Agent, or Firm*—Hovey, Williams, Timmons & Collins

[57] ABSTRACT

Stable, aqueous detergent-iodine germicidal use compositions and concentrates adapted for application to animal or human skin are provided which have desirable detergent:iodine ratios of from about 2-4.5. The compositions and concentrates include a polyethoxylated polyoxypropylene block copolymer (poloxamer) as the complexing agent, wherein the polyoxypropylene moiety has an average molecular weight of at least 2600 and a polyoxyethylene content of from about 30%-75% by weight, in combination with from about 0.1%-5% by weight average available iodine on a nominal basis. Use of the defined class of poloxamers allows formulation of both high and low temperature stable compositions and concentrates. Other ingredients such as emollients, buffering agents and viscosity improvers can also form a part of the use compositions and concentrates.

43 Claims, No Drawings

5,368,868

GERMICIDAL DETERGENT-IODINE COMPOSITIONS HAVING REDUCED DETERGENT CONTACT

This application is a continuation of application Ser. No. 07/947,041, filed Sep. 18, 1992, now abandoned.

BACKGROUND OF THE INVENTION

1. Field of the Invention

The present invention is broadly concerned with improved, stable, detergent-iodine germicidal compositions and concentrates that can be diluted to provide such compositions, useful for topical applications to the skin of human or animals, having relatively low detergent/average available iodine ratios. More particularly, it is concerned with such concentrates and use compositions wherein the detergent/average available iodine ratio ranges from about 2:1 to about 4.5:1, and wherein the detergent fraction comprises a polyoxypropylene-polyoxyethylene block copolymer having a central polyoxypropylene (POP) molecular weight of at least about 2600 and a polyoxyethylene (POE) content on the order of 30%–75% by weight. Use of specific detergents of this character has been found to yield low ratio, high and low temperature stable germicidal use compositions and concentrates.

2. Description of the Prior Art

Germicidal detergent-iodine products designed for topical application to the skin have long been available. These formulations are used primarily in products such as pre-operative antiseptic preparations, hand cleaners and in bovine teat dips for mastitis prevention. Apart from complexed detergent-iodine, these products typically include variable amounts of additives to provide pH control, emolliency, viscosity, and in some cases a colorant.

U.S. Pat. No. 3,728,449 describes a wide range of detergent-iodine germicidal compositions specifically adapted for application to the teats of milk animals for the control and prevention of mastitis. A number of ethoxylated nonionic iodine complexing agents are disclosed as being effective in the '449 patent, at a minimum ratio of 5 parts complexing agent to each part of average available iodine. Among the complexing agents described in this patent are the nonylphenol ethoxylates, polyalkylene glycol ethers, polyoxyethylene sorbitan monolaurate and monopalmitate, polyvinylpyrrolidone and polyethoxylated polyoxypropylenes. This latter type of complexing agent is referred to in the art as a "poloxamer", which is in the form of a block copolymer based on a central polyoxypropylene moiety with polyoxyethylene groups at the respective ends of the central moiety. There are a wide range of commercially available poloxamers having central moieties ranging in molecular weight from about 1000 to 4000, and containing polyoxyethylene contents on the order of 10%–80% by weight of the total weight of the poloxamer.

In order to be dependable and useful to an end user, detergent-iodine germicidal use compositions and concentrates must be stable (i.e., remain homogeneous) over a wide range of temperature. If stability is lost, and the products separate, the utility of the compositions is significantly degraded and they can present a potential hazard to the user. Generally speaking, stability in this context means that a given product must remain completely homogeneous after extended storage (e.g., 1 week) at temperatures as low as 2° C. (which may be experienced in cold warehouse storage areas) or as high as 40° C., which can occur during transport in closed vehicles. Furthermore, although a given product may separate when frozen, especially after undergoing several freeze-thaw cycles, it must be readily reconstitutable as a homogeneous mixture upon simple shaking or mixing.

In addition, all detergent-iodine formulations have some iodide ion present, which can vary as desired from relatively high concentrations described in U.S. Pat. No. 3,028,299 to relatively low, stabilized values taught in U.S. Pat. No. 4,271,149. In general, iodide ion levels range from about 0.3–1 part iodide per part of iodine in prior formulations.

As indicated above, detergent-iodine products designed for topical application to the skin are normally formulated with an amount of emollient. The most common emollients employed are glycerin, lanolin and its derivatives, sorbitol, fatty acid esters of polyhydroxylated compounds, and propylene glycol. These emollients are used at levels ranging from below 1% to as much as 10% in use compositions. Glycerin is the most widely used emollient in bovine teat dips and is also used extensively at low levels in human topical detergent-iodine and povidone-iodine formulations.

Another desirable functional characteristic for detergent-iodine germicidal compositions designed for topical application, is the ability to spread evenly on the skin and not drain off so rapidly as to prevent insufficient germicidal contact time. Many of the usual ingredients in detergent-iodine products contribute to viscosity. However, it is common for topical products to be formulated with a specific thickener to provide added viscosity. There are many viscosity modifiers compatible with detergent-iodine systems, such as carboxymethylcellulose derivatives, polyacrylate derivatives, alginates, xanthates and polysaccharides. These are typically used at levels below 1% by weight in a final use composition. These types of ingredients, properly selected, have an insignificant effect on the homogeneity of a given use composition. On the other hand, where dilutable concentrates are desired, viscosity-modifying additives can become a problem and special care must be taken in the selection of specific agents and their levels of use in concentrates.

As explained above, the prior art is replete with examples of detergent-iodine formulations having relatively high detergent/average available iodine ratios in excess of 5:1. U.S. Pat. No. 3,728,449 describes a single example at a ratio of 5:1, which makes use of PVP as a complexing agent. The next lowest ratio example in this patent uses a nonylphenol ethoxylate at a ratio of 7.5:1. Example IIID describes a composition made up to include 5 parts of a poloxamer (Pluronic P123), but the total detergent/average available iodine ratio of this example is 8:1.

There are a number of potential advantages in the use of very low detergent/average available iodine ratios in germicidal iodine concentrates and use compositions designed for skin or tissue application. For example, in a low ratio product of this type, there would be less organic matter to react with the iodine, thereby rendering such compositions more stable relative to the labeled or nominal available iodine content. Another advantage is that reduced amounts of detergent would be expected to be less irritating to the skin and would accordingly require a lesser amount of emollient. Compositions with lower detergent/average available iodine ratios could be formulated to have higher, and more stable, free or uncomplexed iodine levels. The use of minimal amounts of detergent also would allow for the possibility of reduced water content in concentrates, thereby correspondingly reducing packaging, shipment and storage costs.

U.S. Pat. No. 2,759,869 describes acid compositions designed for significant dilution before use. As acid concentrates, especially with added alcohol, the examples described in this patent can include detergent/average available iodine ratios less than 5:1. However, these compositions have a very low pH on the order of 0–1, and as such are not suited for application to skin or tissues; rather, they are used as hard surface germicides after dilution at about 1:100 or more.

U.S. Pat. No. 2,759,869 describes the use of a poloxamer, Pluronic L-62, which may yield clear solutions at a ratio below 5:1, particularly in very low pH acid formulations. However, it has been found that Pluronic L-62 (having a polyoxypropylene average molecular weight of about 1700 and a polyoxyethylene content of about 20%) and its equivalents are not acceptable as an iodine complexing agent at 4.5:1 (or lower ratio) and average available iodine levels at the pH required for a germicide adapted for use on human or animal skin, in that it separates at temperatures below 22° C. Similarly, 5:1 ratio compositions described in U.S. Pat. No. 3,028,299 do not have the stability necessary for final marketable product.

Accordingly, there is a real and unsatisfied need in the art for improved, low ratio detergent-iodine use compositions (and their dilutable concentrate counterparts) which have the requisite stability and germicidal utility and which can be applied directly to animal or human skin.

SUMMARY OF THE INVENTION

The present invention overcomes the problems outlined above and provides desirable aqueous, stable, low-ratio, poloxamer-iodine complexed use compositions and concentrates for skin or tissue application. The present invention is predicated in part upon the discovery that a certain limited class of poloxamers can be used as a part of such low-ratio formulations without sacrificing stability or other desirable qualities.

Generally speaking, the use compositions of the invention include from about 0.1%–1.3% by weight average available iodine on a nominal basis, and from about 2 to about 4.5 parts of polyethoxylated polyoxypropylene (poloxamer) complexing agent per part of average available iodine, wherein the polyoxypropylene moiety has an average molecular weight of at least about 2600 and a polyoxyethylene content of from about 30%–75% by weight. The pH of the use compositions is adjusted to a level of from about 2–7.

In preferred forms, the poloxamer is selected such that the polyoxypropylene moiety thereof has an average molecular weight of from about 2600–4000, and more preferably from about 3000–4000, whereas the polyoxyethylene content may range from about 40%–70% by weight for certain types of compositions, and from about 30%–50% by weight, or 30%–40% by weight, for other types of compositions within the scope of the invention. The pH of the aqueous use compositions is advantageously from about 2–6.5, and may be in the range of from about 2–4 or 4–6.5, depending upon the composition in question; generally, lower pHs give more stable compositions. The compositions should also contain from about 0.2–1, and more preferably from about 0.3–0.5, parts iodide per part of available iodine.

The compositions of the invention may also include a number of other ingredients, for example an emollient which would typically be present at a level from about 0.1%–10% by weight, and more preferably from about 1%–5% by weight. Suitable emollients may be selected from the group consisting of glycerin, sorbitol, propylene glycol, lanolin, ethoxylated lanolin derivatives, and mixtures thereof. Likewise, a buffering agent such as those selected from the group consisting of the salts of citric, lactic, acetic and phosphoric acids and mixtures thereof would also normally be present for pH control, typically at a level from about 0.1%–1% by weight, and more preferably from about 0.2%–0.5% by weight.

The invention also comprehends aqueous germicidal concentrates adapted for dilution with water to form a resultant use composition. In such a case, the concentrate would comprise from about 1%–5% by weight average available iodine on a nominal basis, and from about 2–4.5 parts of poloxamer complexing agent of the type described above per part of average available iodine. Other variable constituents of the concentrate would correspond, in appropriately higher amounts, to those described above in connection with the final use compositions.

The compositions of this invention are unique in that they represent the most efficient iodine complexors-solubilizers ever described. There are no other known organic substances, of any type, that can solubilize iodine at such low complexor/iodine ratios in compositions suitable for application to skin tissue. Indeed, the only substance that is somewhat more efficient at solubilizing iodine on a weight basis, is iodide ion $(I^-)$ itself. As little as about 1:1 iodide/iodine can be used to solubilize iodine in water, such as the well known 2% iodine topical solution (USP), but such preparations are of little practical use today, in that they are regarded as being too irritating to skin tissue.

DETAILED DESCRIPTION OF THE PREFERRED EMBODIMENTS

The preferred poloxamers useful in the invention can be derived from any commercial source. However, the appropriate Pluronic poloxamers commercialized by BASF Chemical Co. have been found to be particularly suitable, so long as members of this family are selected having the requisite polyoxypropylene molecular weight (POP Mol. Wt.) and polyoxyethylene content (POE % By Wt.). Pluronic poloxamers are described in a BASF brochure entitled "Typical Properties of Block Copolymer Surfactants", such brochure being incorporated by reference herein. It should be understood in this respect that poloxamers having a POP molecular weight above about 4500 are not presently available, but that such species would be expected to be useful in the context of the present invention. Not every member of the defined class of poloxamers of the present invention is necessarily suitable for every low ratio poloxamer to average available iodine, at every iodine level. Generally speaking, with end use compositions, a somewhat higher ratio of poloxamer to average available iodine is required at the 0.1% available iodine level, as compared with the minimal ratios required at higher available iodine levels. However, all members of this defined class which have been studied can be used at some ratio at about 4.5:1 or below. Finally, use can be made of other types of complexing agents in combination with one or more members of the defined class of poloxamers. For example, complexing agents such as alcohol ethoxylates, nonylphenol ethoxylates, and polyvinylpyrrolidone can be used in conjunction with the defined poloxamers, particularly where the latter are present as the major complexor component.

Furthermore, it will be understood that most detergent-iodine compositions formulated for skin application may contain a minimum of about 0.1% available iodine and a maximum of about 1.3% available iodine, and usually this maximum can be considered to be on the order of about 1% available iodine. There are detergent-iodine compositions, which have nominal available iodine values, but in fact contain significantly more average available iodine. For example, a nominal 1% available iodine product may in fact contain as much as 1.2% or even 1.25% by weight available iodine. This occurs because almost every composition will contain an "overage" of available iodine when manufactured, so as to allow for iodine loss over the life of the product. As such, it will be understood that reference herein to average available iodine on a nominal basis covers such excess amounts.

The compositions of the invention will also contain iodide which can usually vary depending on the formulation, from about 0.2-1 part of iodide ion per part of average available iodine. However, the novel compositions of the invention are not iodide dependent insofar as the amount of iodide is concerned. The amount of iodide present can in some cases have an effect on the stability and homogeneity of a given use composition. However, the novel poloxamer:iodine rations can accommodate the levels of iodide previously utilized in the art.

The presence of buffering agent(s) is generally desirable in compositions and concentrates in accordance with the present invention, and those salts described previously are preferred. Sodium citrate is the most preferred buffering agent. The amount of buffering agent employed in a particular formulation is chosen on the basis of pH stability characteristics determined over a period of time. In use compositions, the small amount of buffering agent present has little or no effect on product homogeneity and stability. In concentrates, however, where the buffering agents are present at higher levels and the water content is significantly lower, the choice of buffering agent can make a significant difference.

The compositions of the invention can also include viscosity agents commonly employed in prior formulations. Here again, the selection and amount of such agent(s) is dependent upon the particular characteristics desired for a given formulation, and whether the composition is in dilute form for end use, or is sold as a concentrate.

The compositions of the invention can also include small amounts of solvents such as alcohols and glycols, which can function to modify viscosity and to aid in the preparation of concentrates.

The following examples describe certain preferred compositions and concentrates in accordance with the invention, as well as methods of preparing and stability testing these formulations. It should be understood that the examples are provided by way of illustration only, and nothing therein should be taken as a limitation upon the overall scope of the invention.

EXAMPLE 1

A series of aqueous detergent-iodine compositions in accordance with the invention were prepared, each including 4.5% by weight of a poloxamer, an average available iodine content of about 1% (thereby giving a poloxamer:available iodine ratio of 4.5), 0.4% by weight iodide, 2.0% by weight glycerine, and 0.5% by weight sodium citrate buffer to give an adjusted pH of about 5. The balance of the compositions was made up of water. In some samples, the poloxamer used had proper molecular weight and percentage polyoxyethylene values in accordance with the invention, and in other samples, different types of poloxamers were used.

Each sample was prepared by mixing an appropriate commercial Pluronic poloxamer (or a mixture of commercial grades to achieve intermediate value poloxamers) with an aqueous iodine concentrate containing approximately 57% by weight iodine and 20% by weight iodide as sodium iodide. A small amount of water was then added followed by the glycerine and sodium citrate buffer. After a small amount of mixing, the remaining formula amount of water was added. After formulation, the homogeneity of the compositions was observed at room temperature, and portions of each sample were tested for high and low temperature stability. Specifically, in the low temperature stability test, the respective samples were placed in a refrigerator at 2° C. for one week, and in the high temperature test, the samples were placed in a constant temperature 40° C. oven. At the end of the test week, both low and high temperature test samples were observed for precipitation and cloudiness; any exhibiting undue cloudiness or precipitation were rejected.

The following Table 1 sets forth the poloxamer molecular weight and percentage polyoxyethylene for the test samples, as well as the results of the stability tests, where "O.K." represents an acceptable product and "X" represents an unacceptable product.

TABLE 1

| Sample # | POP Mol. Wt.[1] | POE %[2] | Stability |
|---|---|---|---|
| 1 | 2600 | 50 | O.K. |
| 2 | 3200 | 30 | O.K. |
| 3 | 3200 | 40 | O.K. |
| 4 | 3200 | 50 | O.K. |
| 5 | 4000 | 30 | O.K. |
| 6 | 4000 | 70 | O.K. |
| 7 | 1300 | 40 | X |
| 8 | 1700 | 20 | X |
| 9 | 1700 | 40 | X |
| 10 | 1700 | 50 | X |
| 11 | 1700 | 80 | X |
| 12 | 2100 | 50 | X |
| 13 | 2300 | 40 | X |
| 14 | 2300 | 50 | X |
| 15 | 2300 | 70 | X |

[1] POP Mol. Wt. = the average molecular weight of the central polyoxypropylene group of the poloxamer block copolymer
[2] POE % = the average polyoxyethylene content of the poloxamer block copolymer, based upon total weight of the copolymer, i.e., 50% = about 50% by weight of the total poloxamer constitutes POE The above data demonstrates that the an average POP molecular weight on the order of about 2500 up to about 4000, together with a POE content of from about 25%-75% by weight, is important in obtaining a stable product having a relatively low poloxamer:available iodine ratio.

EXAMPLE 2

In another series of similar tests, aqueous detergent-iodine compositions were prepared having varying compositions with different levels of poloxamer, emollient, and pH, and the above-described stability tests were performed. Each sample contained an appropriate poloxamer, an average available iodine content of about 1.0%, and 0.5% by weight sodium citrate buffer; the samples were made by the steps outlined in Example 1, and the balance of each composition was water. The results of these tests are set forth in Table 2.

TABLE 2

| Sample # | POP Mol. Wt. | POE % | Wt. % Poloxamer | Iodide | Glycerine % By Wt. | pH | Stability |
|---|---|---|---|---|---|---|---|
| 1 | 3200 | 50 | 4.5 | 0.4 | 2 | 3 | O.K. |
| 2 | 3200 | 50 | 4.5 | 0.4 | 2 | 4 | O.K. |
| 3 | 3200 | 50 | 4.5 | 0.4 | 10 | 5 | O.K. |
| 4 | 3200 | 50 | 2.5 | 0.4 | 0 | 5 | O.K. |
| 5 | 3200 | 50 | 2.5 | 0.4 | 5 | 5 | O.K. |
| 6 | 3200 | 50 | 2.5 | 0.4 | 2 | 5 | O.K. |
| 7 | 3200 | 40 | 4.5 | 0.4 | 2 | 6 | O.K. |
| 8 | 3200 | 40 | 4.5 | 0.4 | 2 | 7 | O.K. |
| 9 | 3200 | 40 | 3.5 | 0.4 | 0 | 5 | O.K. |
| 10 | 3200 | 30 | 3.0 | 0.4 | 5 | 5 | O.K. |
| 11 | 3200 | 50 | 4.5 | 1.0 | 10 | 5 | O.K. |

This example demonstrates that emollient content, iodide and pH levels can be varied over wide ranges, while still providing acceptable compositions having low detergent-iodine ratios.

EXAMPLE 3

In this test, a number of aqueous detergent-iodine compositions were prepared and stability tested as set forth in Example 1. In each case, the poloxamer had a POP mol. wt. of 3200, and a POE content of 50% (except Sample #2 which had a POE content of 40%); all had an average available iodine content of 0.5% by weight, an iodide content of 0.2% by weight, a sodium citrate content of 0.25% by weight, and a pH of about 5. The amounts of poloxamer and glycerine were varied, but in all cases, the balance of the respective compositions was made up of water. These results are set forth below.

TABLE 3

| Sample # | Wt. % Poloxamer | Poloxamer/ Av. $I_2$ | Glycerine % By Wt. | Stability |
|---|---|---|---|---|
| 1 | 1.25 | 2.5 | 2 | O.K. |
| 2 | 1.25 | 2.5 | 2 | O.K. |
| 3 | 1.0 | 2.0 | 5.0 | O.K. |
| 4 | 1.0 | 2.0 | 10 | O.K. |

EXAMPLE 4

A further series of compositions were prepared and stability tested, using various commercial grade poloxamers (or mixtures thereof) at different levels, with an average iodine content of about 0.25% by weight, 0.2% by weight sodium citrate buffer and with a pH of about 5. The compositions were made and tested as in Example 1 and the balance of each composition was water. The data from this test series is set forth in Table 4.

TABLE 4

| Sample # | POP Mol. Wt. | POE % Wt. | Wt. % Poloxamer | Poloxamer/Av. $I_2$ | Iodide % By Wt. | Glycerine % By Wt. | Stability |
|---|---|---|---|---|---|---|---|
| 1 | 3200 | 50 | 0.625 | 2.5 | 0.1 | 1 | O.K. |
| 2 | 4000 | 30 | 0.625 | 2.5 | 0.1 | 1 | O.K. |
| 3 | 3200 | 50 | 0.5 | 2.0 | 0.1 | 10 | O.K. |
| 4 | 4000 | 30 | 0.5 | 2.0 | 0.1 | 10 | O.K. |
| 5 | 4000 | 30 | 0.625 | 2.5 | 0.25 | 1 | O.K. |

EXAMPLE 5

In this example, a series of low ratio, pH=5 aqueous poloxamer detergent-iodine compositions containing 0.25% by weight average available iodine and 0.2% by weight sodium citrate buffer were prepared and stability tested as set forth in Example 1; the balance of all compositions was water. The results are set forth in the following table, and should be compared with the results of Table 4.

TABLE 5

| Sample # | POP Mol. Wt. | POE % Wt. | Wt. % Poloxamer | Poloxamer/Av. $I_2$ | Iodide % By Wt. | Glycerine % By Wt. | Stability |
|---|---|---|---|---|---|---|---|
| 1 | 2300 | 50 | 0.625 | 2.5 | 0.1 | 1 | X |
| 2 | 2300 | 50 | 1.0 | 4 | 0.1 | 1 | X |
| 3 | 2300 | 50 | 1.125 | 4.5 | 0.1 | 10 | X |
| 4 | 1700 | 50 | 1.0 | 4 | 0.1 | 1.0 | X |

As set forth above, the approximate 0.25% available iodine compositions having POP molecular weights of less than about 2600 were unsatisfactory, whereas those compositions set forth in Table 4 made with higher molecular weight POP moieties were stable.

EXAMPLE 6

Another series of compositions were prepared, all having 0.45% by weight poloxamer, an available iodine content of about 0.1% by weight, an iodide content of about 0.04% by weight and a pH of about 5. These compositions were made and tested as set forth in Example 1, with the balance of each composition being water.

TABLE 6

| Sample # | POP Mol. Wt. | POE % By Wt. | Poloxamer/ Av. I$_2$ | Glycerine % By Wt. | Sodium Citrate % By Wt. | Stability |
|---|---|---|---|---|---|---|
| 1 | 3200 | 50 | 4.5 | — | 0.1 | O.K. |
| 2 | 3200 | 50 | 4.5 | 1 | 0.1 | O.K. |
| 3 | 4000 | 30 | 4.5 | 2 | 0.1 | O.K. |
| 4 | 4000 | 50 | 4.5 | — | 0.1 | O.K. |
| 5 | 4000 | 50 | 4.5 | 5 | 0.1 | O.K. |
| 6 | 3200 | 50 | 4.5 | — | 0.05 | O.K. |

EXAMPLE 7

A series of aqueous detergent-iodine compositions were made using a number of different poloxamers all having POP molecular weights below 2600. In all cases, 0.45% by weight poloxamer was used, and the compositions contained about 0.1% by weight available iodine, 0.04% by weight iodide, 0.2% by weight glycerine and 0.05% by weight sodium citrate; all compositions had a pH of 5. All of the compositions were unstable either at room temperature or at cooler temperatures. In this series of compositions, poloxamers having the following POP molecular weight/POE percentage distributions were used: 1300/40%; 1700/20%; 1700/40%; 1700/50%; 1700/80%; 2100/50%; 2300/40; and 2300/70%.

EXAMPLE 8

As described previously, the iodine concentration of iodine compositions adapted for topical application to the skin is predominantly in the range of from about 0.1%–1% average available iodine. It is frequently desired to make concentrates of such compositions, suitable for dilution prior to use. Such concentrates offer the advantages of minimizing manufacturing, packaging, shipping and storage costs. The detergent-iodine compositions of the invention are particularly suited for such concentrates, since they use a minimum total solids in the concentrate and therefore maximize the amount of water that can be present. Without sufficient water, many concentrates are excessively viscous, and it may be difficult to provide proper pH buffering.

Generally speaking, concentrates usually contain from about 1%–5% by weight of available iodine, and are usually formulated to provide 4, 8 and 16 times the original concentrate volume, after dilution with an appropriate amount of water.

A composition adapted for dilution with 3 parts of water to yield a 1% available iodine level can be formulated using a poloxamer having a POP mol. wt./POE % by weight value of 3200/50% at a level of 12%; 4.3% by weight average available iodine; an iodide content of 1.5% by weight and a pH 3 citrate buffer content of 0.5% by weight. These compositions are formulated as set forth in Example 1.

Another composition for use at the same 1+3 dilution factor to yield a 1% nominal available iodine level, can be formulated using a poloxamer having a POP mol. wt/POE % by weight value of 3200/54% at a level of 16%; 4.1% by weight average available iodine; an iodide content of 1.4% by weight; 19% by weight glycerine; and a pH 5 citrate buffer content of 0.5% by weight. The balance of this composition is water.

The following compositions shown below can be diluted with 7 and 15 parts of water to yield 0.1% average available iodine. The compositions are prepared as set forth in Example 1, and the balance thereof in each case is water.

TABLE 8

| Sample # | POP Mol. Wt. | POE % Wt. | Wt. % Poloxamer | Ratio | Av. I$_2$ | Iodide % By Wt. | Glycerine % By Wt. | Sodium Citrate Buffer | pH |
|---|---|---|---|---|---|---|---|---|---|
| 1 | 3200 | 50 | 3.6 | 4.5 | 0.8 | 0.32 | — | 0.8 | 5 |
| 2 | 3200 | 50 | 3.6 | 4.5 | 0.8 | 0.32 | 8 | 0.8 | 5 |
| 3 | 4000 | 30 | 3.6 | 3.5 | 0.8 | 0.32 | 16 | 0.8 | 5 |
| 4 | 3200 | 50 | 7.2 | 4.5 | 1.6 | 0.64 | 16 | 1.6 | 5 |
| 5 | 3200 | 50 | 7.2 | 4.5 | 1.6 | 0.64 | — | 1.6 | 5 |

As can be seen from the foregoing examples, the present invention provides stable, improved poloxamer iodine germicidal use compositions and concentrates of varying makeup. The following tables respectively for the use compositions and concentrates set forth the types of ingredients contemplated, as well as approximate ranges and preferred use levels thereof.

TABLE 9

| | Use Compositions | | |
|---|---|---|---|
| | Ingredients | Broad Range | Preferred Range |
| 1. | Parts Poloxamer per Part Available I$_2$ | 2–4.5 | 2.5–4.5 |
| | a. POP Mol. Wt. | ≧2600 | 3200–4000 |
| | b. POE % By Wt. | 30–75 | 40–70 |
| 2. | Average Available I$_2$ % By Wt. | 0.1–1.3% | 0.1–1% |
| 3. | Parts Iodide Per Part Available I$_2$ | 0.2–1 | 0.3–0.5 |
| 4. | Emollient % By Wt. | 0–10% | 1–5% |
| 5. | Buffering Agent % By Wt. | 0.1–1% | 0.2–0.5% |
| 6. | Water % By Wt. | Q.S.* | Q.S.* |
| 7. | pH | 2–7 | 4–6.5 |

*Quantity Sufficient to bring total to 100%.

TABLE 10

| | Concentrates | | |
|---|---|---|---|
| | Ingredients | Broad Range | Preferred Range |
| 1. | Parts Poloxamer per Part Available I$_2$ | 2–4.5 | 2.5–4.5 |
| | a. POP Mol. Wt. | ≧2600 | 3200–4000 |
| | b. POE % By Wt. | 30–75 | 40–70 |
| 2. | Average Available I$_2$ % By Wt. | 1–5% | — |
| 3. | Parts Iodide Per Part Available I$_2$ | ≧0.2 | 0.3–0.5 |

TABLE 10-continued

| | Ingredients | Concentrates Broad Range | Preferred Range |
|---|---|---|---|
| 4. | Emollient % By Wt. | 0–32% | 8–16% |
| 5. | Buffering Agent % By Wt. | 0.2–2% | 0.5–1.5% |
| 6. | Water % By Wt. | Q.S.* | Q.S.* |
| 7. | pH | 2–7 | 3–6.5 |

*Quantity Sufficient to bring total to 100%

I claim:

1. An aqueous detergent-iodine germicidal use composition comprising from about 0.1%–1.3% by weight average available iodine on a nominal basis, from about 2 to about 4.5 parts of complexing agent per part of available iodine, said complexing agent including a polyethoxylated polyoxypropylene having a polyoxypropylene moiety with an average molecular weight of at least about 2600 and a polyoxyethylene content from about 30%–75% by weight, said composition having a pH of from about 2–7.

2. The composition of claim 1, said polyoxypropylene moiety having an average molecular weight of from about 2600–4000.

3. The composition of claim 2, wherein said average molecular weight is from about 3000–4000.

4. The composition of claim 1, there being from about 2 to about 3.5 parts of complexing agent per part of available iodine.

5. The composition of claim 1, said polyoxyethylene content being from about 40%–70% by weight.

6. The composition of claim 5, said polyoxyethylene content being from about 50% by weight.

7. The composition of claim 1, said polyoxyethylene content being from about 30%–50% by weight.

8. The composition of claim 7, said polyoxyethylene content being from about 30%–40% by weight.

9. The composition of claim 1, said pH being from about 4–6.5.

10. The composition of claim 9, said pH being from about 2–4.

11. The composition of claim 1, including a quantity of emollient therein.

12. The composition of claim 11, said emollient being present at a level of from about 0.1%–10% by weight.

13. The composition of claim 11, said emollient being selected from the group consisting of glycerin, sorbitol, propylene glycol, lanolin, ethoxylated lanolin derivatives, and mixtures thereof.

14. The composition of claim 1, including from about 0.2–1 part of iodide ion per part of available iodine.

15. The composition of claim 1, including a buffering agent.

16. The composition of claim 15, said buffering agent being selected from the group consisting of the salts of citric, lactic, acetic and phosphoric acids and mixtures thereof.

17. The composition of claim 16, said buffering agent being sodium citrate.

18. The composition of claim 15, said buffering agent being present at a level of from about 0.1%–1% by weight.

19. The composition of claim 1, there being from about 2 to about 3.5 parts of complexing agent per part of available iodine, and said pH being 4–6.5.

20. The composition of claim 1, said polyoxyethylene content being from about 30% to about 40% by weight, said pH being from about 4–6.5.

21. The composition of claim 1, said average molecular weight being from about 3000 to about 4000, and said pH being from about 4–6.5.

22. The composition of claim 1, said polyoxyethylene content being about 50%, and said pH being from about 4–6.5.

23. The composition of claims 1, 2, 3, 4, 5, 6, 7, 8, 9, 10, 12, 13, 14, 15, 16, 17, 18, 19, 20, 21 or 22, including an emollient therein.

24. The composition of claims 1, 2, 3, 4, 5, 6, 7, 8, 9, 10, 13, 14, 15, 16, 17, 18, 19, 20, 21 or 22, including from about 0.1% to about 10% by weight emollient therein.

25. The composition of claims 1, 2, 3, 4, 5, 6, 7, 8, 9, 10, 11, 12, 13, 14, 15, 16, 17, 19, 20, 21 or 22, including from about 0.2 to about 1 part of iodide ion per part of available iodine.

26. The composition of claims 1, 2, 3, 4, 5, 6, 7, 8, 9, 10, 11, 12, 13, 14, 16, 17, 18, 19, 20, 21 or 22, including a buffering agent.

27. The composition of claims 1, 2, 3, 4, 5, 6, 7, 8, 9, 10, 11, 12, 13, 14, 15, 16, 17, 18, 19, 20, 21 or 22, said complexing agent consisting essentially of polyethoxylated polyoxypropylene.

28. An aqueous detergent-iodine germicidal concentrate adapted for dilution with water to form a stable use composition, said concentrate comprising from about 1%–5% by weight average available iodine on a nominal basis, and from about 2–4.5 parts of complexing agent per part of available iodine, said complexing agent including a polyethoxylated polyoxypropylene having a polyoxypropylene moiety with an average molecular weight of at least about 2600 and a polyoxyethylene content from about 30%–75% by weight, said concentrate having a pH of from about 2–7.

29. The concentrate of claim 28, said polyoxypropylene moiety having an average molecular weight of from about 2600–4000.

30. The concentrate of claim 28, said polyoxyethylene content being from about 40%–70% by weight.

31. The concentrate of claim 28, said pH being from about 4–6.5.

32. The concentrate of claim 28, including a quantity of emollient therein.

33. The concentrate of claim 32, said emollient being present at a level of from about 8%–16% by weight.

34. The concentrate of claim 32, said emollient being selected from the group consisting of glycerin, sorbitol, propylene glycol, lanolin, ethoxylated lanolin derivatives, and mixtures thereof.

35. The concentrate of claim 28, including from about 0.2–1 part of iodide ion per part of available iodine.

36. The concentrate of claim 28, including a buffering agent.

37. The concentrate of claim 36, said buffering agent being selected from the group consisting of the salts of citric, lactic, acetic and phosphoric acids and mixtures thereof.

38. The concentrate of claim 37, said buffering agent being sodium citrate.

39. The concentrate of claim 38, said buffering agent being present at a level of from about 0.2%–2% by weight.

40. The concentrate of claim 38, said concentrate being adapted for dilution with water at a level of from about 4–16 parts of water per part of concentrate.

41. The concentrate of claim 28, said complexing agent consisting essentially of polyethoxylated polyoxypropylene.

42. In an aqueous detergent-iodine germicidal use composition including from about 0.1%-1.3% by weight average available iodine on a nominal basis, and a complexing agent for said available iodine, the improvement which comprises a stable composition having a ratio of complexing agent to average available iodine of from about 2:1 to about 4.5:1.

43. The composition of claim 42, said complexing agent including a polyethoxylated polyoxypropylene having a polyoxypropylene moiety with an average molecular weight of at least about 2,600 and a polyoxyethylene content from about 30%-75% by weight, said stable composition having a pH of from about 2-7.

* * * * *

UNITED STATES PATENT AND TRADEMARK OFFICE
CERTIFICATE OF CORRECTION

PATENT NO. : 5,368,868
DATED : November 29, 1994
INVENTOR(S) : Murray W. Winicov It is certified that error appears in the above-indentified patent and that said Letters Patent is hereby corrected as shown below:

On the title page item [54], "contact" should read --content--.

Signed and Sealed this

Fourteenth Day of March, 1995

Attest:

BRUCE LEHMAN

*Attesting Officer*    *Commissioner of Patents and Trademarks*